United States Patent [19]
Yoshida et al.

[11] Patent Number: 5,409,956
[45] Date of Patent: Apr. 25, 1995

[54] INDAN DERIVATIVE AND THROMBOXANE ANTAGONIST CONTAINING THE SAME

[75] Inventors: Kiyoshi Yoshida; Yoshiaki Yamaji; Tadashi Kurimoto; Ryuichi Sato; Motoki Torizuka, all of Konan, Japan

[73] Assignee: Zeria Pharmaceutical Co., Ltd., Tokyo, Japan

[21] Appl. No.: 107,823

[22] PCT Filed: Feb. 28, 1992

[86] PCT No.: PCT/JP92/00236

§ 371 Date: Aug. 30, 1993

§ 102(e) Date: Aug. 30, 1993

[87] PCT Pub. No.: WO92/15558

PCT Pub. Date: Sep. 17, 1992

[30] Foreign Application Priority Data

Mar. 1, 1991 [JP] Japan .................. 3-057619

[51] Int. Cl.$^6$ .................. A01N 37/12; C07C 311/00
[52] U.S. Cl. .................. 514/562; 514/510; 514/601; 514/602; 514/603; 514/604; 514/605; 560/10; 562/428
[58] Field of Search .................. 560/10; 562/428; 514/562, 510, 601, 602, 603, 604, 605

[56] References Cited

U.S. PATENT DOCUMENTS

| | | | |
|---|---|---|---|
| 4,820,705 | 4/1989 | Nickl et al. | 514/247 |
| 4,929,754 | 5/1990 | Nickl et al. | 562/428 |
| 5,030,652 | 7/1991 | Iwakuma et al. | 514/510 |
| 5,190,975 | 3/1993 | Iwakuma et al. | 514/562 |

*Primary Examiner*—José G. Dees
*Assistant Examiner*—Dwayne C. Jones
*Attorney, Agent, or Firm*—Bacon & Thomas

[57] ABSTRACT

The present invention relates to indan derivatives represented by the formula (1) or pharmaceutically acceptable salts thereof:

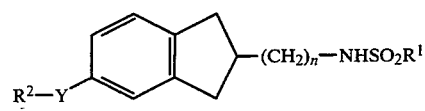

(1)

[wherein $R^1$ represents C1 to C12 alkyl, benzyl, styryl, naphthyl, optionally substituted phenyl or optionally substituted thienyl; $R^2$ represents carboxyl, C1 to C4 alkoxycarbonyl,

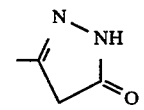

or

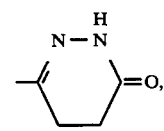

Y represents $-(CH_2)_p-$ (wherein p represents an integer of 0 to 5), $-CO-(CH_2)_q\sim$, $-CH(OH)-(CH_2)_q\sim$, (wherein q represents an integer of 1 to 4, and the symbol $\sim$ represents a linkage to $R^2$), oxymethylene or ethylene; and n represents an integer of 1 to 4]. The compounds according to the present invention potently antagonize the action of thromboxane $A_2$, and therefore useful for the treatment and prevention of diseases caused by thromboxane $A_2$ such as angiosis, vasospasm, asthma and the like.

6 Claims, No Drawings

INDAN DERIVATIVE AND THROMBOXANE ANTAGONIST CONTAINING THE SAME

TECHNICAL FIELD

The present invention relates to novel indan derivatives or salts thereof which are capable of potently antagonizing the action of thromboxane A₂ (hereinafter may be referred to as TXA₂) and are significant in the medical field. More particularly, the present invention relates to indan derivatives or salts thereof which are useful for the treatment and prevention of diseases or diseased states caused by TXA₂, such as thrombosis, vasospasm or asthma, and also to thromboxane antagonists containing the compounds.

BACKGROUND ART

TXA₂ is a metabolite of arachidonic acid widely found in organs of creatures, such as the liver, kidney, lung and the brain, and it is known to have function of strongly coagulating the platelets and contracting the blood vessel ("Cascade of Arachidonic Acid and Drug" by Shozo YAMAMOTO, 1985).

Moreover, it is known that TXA₂ is associated with various diseases such as cardiac infarction, angina pectoris, thrombosis, transient cerebral ischemia, hemicrania, cerebral hemorrhage, cerebral infarction, arteriosclerosis, peripheral circulatory insufficiency or failure, high blood pressure, pulmonary embolism, bronchial asthma, bronchitis, pneumonia, nephritis, hepatitis, and shocks because it strongly contracts the bronchi and the tracheal smooth muscles.

Accordingly, it is expected that effective treatments against the above-mentioned diseases may be obtained by suppressing the action of TXA₂, and many studies have already been reported. For example, Japanese patent publication (Kokoku) 57-35910 discloses 4-(2-phenylsulfonylaminoethyl)phenoxy acetic acid derivatives as compounds which antagonize the action of TXA₂. These compounds, however, are not necessarily satisfactory in terms of the efficacy as pharmaceuticals, lasting ability of the action, adverse side effects and so on.

Under these circumstances, the present inventors have carried out careful studies toward solving the above-mentioned problems, and have found that certain indan derivatives or their salts have a much stronger. TXA₂ antagonizing activity than the above-described 4-(2-phenylsulfonylaminoethyl)phenoxy acetic acid derivatives, leading to the completion of the invention.

DISCLOSURE OF THE INVENTION

According to the present invention, there are provided indan derivatives represented by the formula (1) or pharmaceutically acceptable salts thereof:

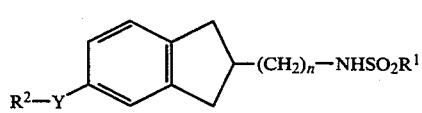

wherein $R^1$ represents C1 to C12 alkyl, benzyl, styryl, naphthyl, optionally substituted phenyl or optionally substituted thienyl; $R^2$ represents carboxyl, C1 to C4 alkoxycarbonyl,

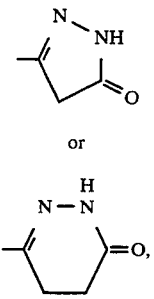

Y represents $-(CH_2)_p-$ (wherein p represents an integer of 0 to 5), $-CO-(CH_2)_q\sim$, $-CH(OH)-(CH_2)_q\sim$, (wherein q represents an integer of 1 to 4, and the symbol $\sim$ represents a linkage to $R^2$), oxymethylene or ethylene; and n represents an integer of 1 to 4.

Moreover, the present invention provides thromboxane antagonists containing, as their active ingredients, the indan derivative of formula (1) above or pharmaceutically acceptable salts thereof.

The term "optionally substituted phenyl" means a phenyl group substituted by C1 to C8 alkyl, C1 to C4 alkoxy, trifluoromethyl, trifluoromethoxy, nitro, amino, nitrile or by a halogen atom at one or two positions, or a phenyl group having no substituent. The term "optionally substituted thienyl" means a thienyl group substituted by C1 to C4 alkyl, C1 to C4 alkoxy, phenylsulfonyl, trifluoromethyl or by a halogen atom at one or two positions, or a thienyl group having no substituent.

BEST MODE FOR CARRYING OUT THE INVENTION

The indan derivatives (1) according to the present invention can be prepared as follows:

First, indan-2-ylalkylcarboxylic acid, which can be prepared by or based on a known method, is converted to indan-2-ylalkylamine by a known method such as a Curtius rearrangement of acylazide or the reduction of carboxylic amide, and is subsequently condensed with a sulfonating agent such as sulfonyl chloride to obtain a sulfonamide derivative represented by formula (2):

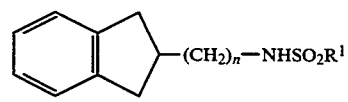

In the above and below-described formulae (1a), (1b), (1c), (1d), (1e), (1f), (2), (3), (4), (5), (6), (7), (8), (9), (10) and (11), the symbol Y' represents $-CO-(CH_2)_q\sim$ (wherein q and $\sim$ individually have the same meaning as defined before), and $R^1$, $R^2$ and n individually have the same meaning as defined before.

Process A

The thus obtained sulfonamide derivative (2) is submitted to a Friedel-Crafts reaction in an inert solvent such as, and preferably, nitrobenzene, carbon disulfide, tetrachloroethane, dichloroethane or dichloromethane, in the presence of an acid chloride preferably acetyl chloride and Lewis acid, and further preferably in the presence of aluminum chloride, stannic chloride, zinc chloride or titanium tetrachloride, in the temperature range of −10° to 50° C., and the reaction product (3) is converted to a compound (4) via a Bayer-Villiger reaction by the use of an organic peracid such as m-chloroperbenzoic acid and perbenzoic acid. The reaction scheme is shown below:

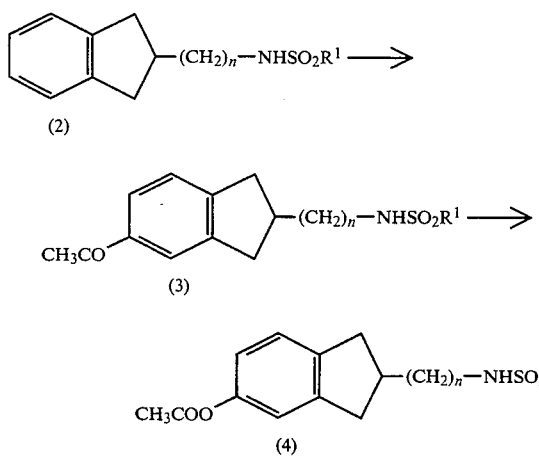

Subsequently, the ester bond of the compound (4) is hydrolyzed to convert the compound (4) to compound (5) with an acid or alkali, and the compound (5) is alkylated, on the position-selective basis, through a reaction with a halide having a desired substituent, to produce the target compound (1a).

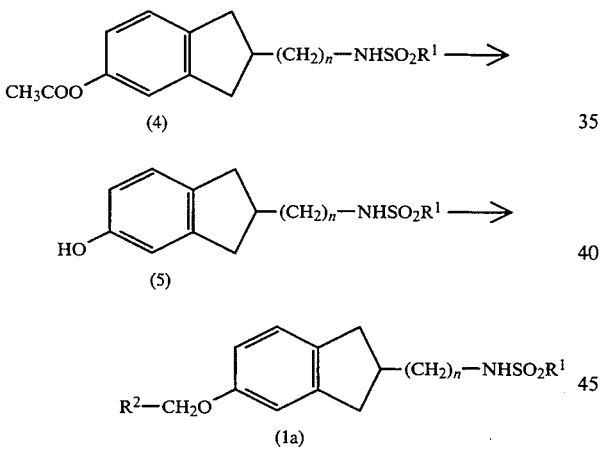

Process B

The methyl indan-2-alkane carboxylate (6) is converted to a compound (7) according to the Process A above, and then submitted to a Bayer-Villiger reaction. Subsequently, the phenol hydroxyl group is protected with a suitable protecting group such as aryl methyl and preferably benzyl, p-methoxybenzyl, 3,4-dimethoxybenzyl, and the ester (6) is hydrolyzed with an acid or alkali. The free carboxylic acid is submitted to a Curtius rearrangement according to the Process A, and the obtained compound (8) is debenzylated to produce a compound (9) at room temperature under reducing conditions in a suitable solvent such as methanol, ethanol, ethyl acetate and tetrahydrofuran, with the use of a metallic catalyst such as palladium, platinum, etc. Next, the phenol hydroxyl group is alkylated with a desired alkylating agent in accordance with the method of Process A for eliminating the amino group, and thus the target compound (1a) is prepared from the obtained compound (10) by the method described above. The reaction scheme is shown below:

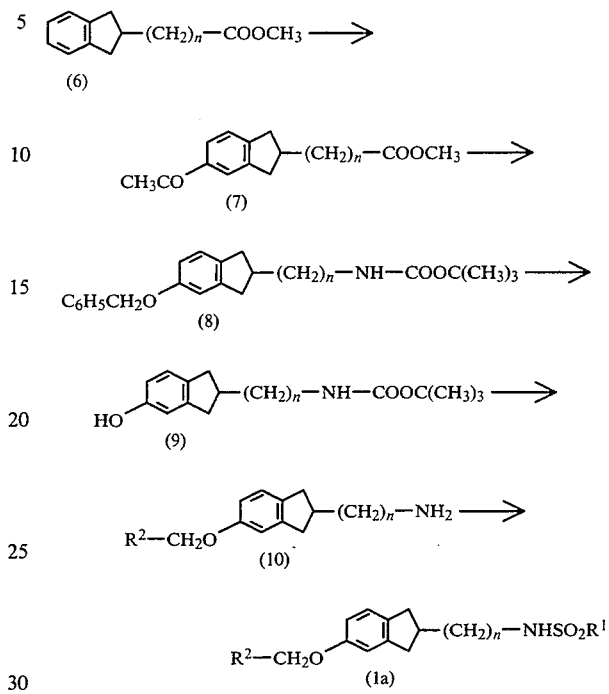

Process C

The target compound (1b) below can be obtained by a known method ("Organic Synthesis", John Willy and Sons, Collective Volume V, 8–11) starting from the compound (3).

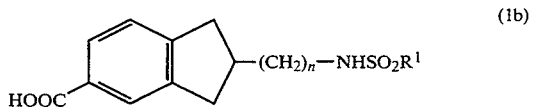

Process D

The compound (2) is condensed with alpha-chloro-alphamethylthio ethyl acetate ester according to a known method ("Chem. Pharm. Bull., 30, 915–921) in the presence of a Lewis acid, and then submitted to the reductive desulfurization to obtain the target compound (1c) below. If desired, the ester is hydrolyzed with an acid or an alkali. Alternatively, the compound (1c) can be obtained by first submitting the indan-2-alkyl carboxylic acid and alpha-chloro-alpha-methylthiosulfate to a Friedel-Crafts reaction, followed by converting the carboxyl group to a sulfonyl amino group.

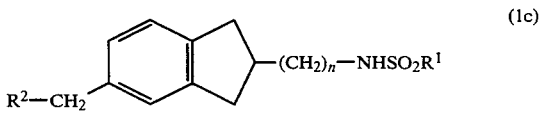

Process E

The target compound (1d) below can be obtained by conducting a Friedel-Crafts reaction using the compound (2) together with a desired acid chloride or acid anhydride according to the Process A.

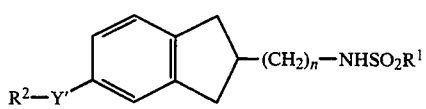

(1d)

Process F

The aldehyde derivative (11) can be synthesized from the compound (2) by a known method (Chem. Ber., 93, 88 (1960)). The aldehyde derivative (11) can be converted to the target compound (1e) shown below by a known reaction such as a Wittig reaction or a Knoevenagel reaction. Moreover, the target compound (1f) also shown below can be obtained by reducing the double bond in compound (1e), if desired. The reaction scheme is shown below.

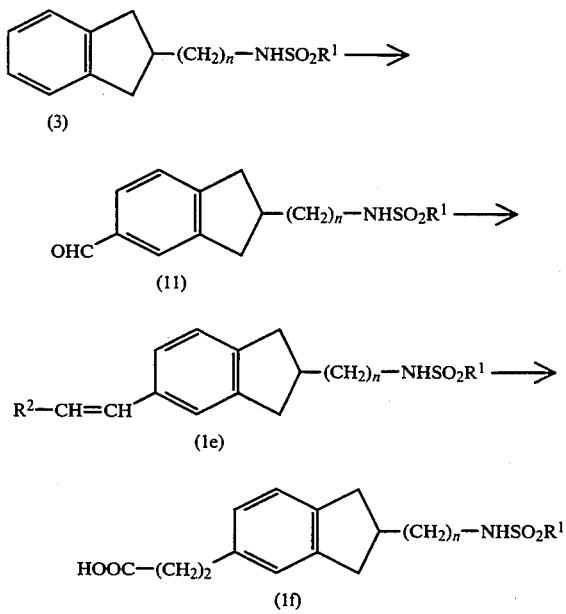

The present compounds (1) embraces two kinds of optical isomers contributed to the asymmetric carbon atom present at the 2-position of the indan skeleton, and their mixture.

The present compound (1) is suited for the pharmaceutical use in the form of a free compound or of a salt of the compound. When the compound is used as a medicine, salts should be pharmaceutically acceptable ones, and include inorganic salts such as sodium salts, potassium salts, calcium salts and magnesium salts, and organic salts such as ammonium salts, pyridine salts, triethylamine salts, ethanolamine salts and basic amino acid salts.

The thus obtained present compounds (1) have excellent $TXA_2$ antagonizing activity as described hereinbelow and are very safe. Therefore, they are useful as a platelet aggregation inhibitory agent and can be utilized for the prevention and treatment of various diseases caused by $TXA_2$, such as embolism and thrombosis, including cerebral thrombosis, coronary thrombosis, pulmonary embolism, chronic arterial obstruction, thromboangiitis and the like. The compounds (1) according to the present invention and their pharmaceutically acceptable salts are also useful for the treatment, alleveation and prevention of miocardial ischemia, angina pectoris, coronary contraction, cerebrovasucular contraction after subarachnoidal hemorrhage, cerebral hemorrhage, asthma, and the like.

The compounds (1) according to the present invention and their pharmaceutically acceptable salts can be administered via oral or non-oral route. For oral route administration, the present compounds can be formed into solid preparations such as tablets, powder and capsules by suitably combining proper additives including vehicles such as lactose, mannitol and corn starch; binders such as cellulose derivatives, gum arabic and gelatin; disintegrators such as carboxymethylcellulose calcium; and lubricants such as talc and magnesium stearate. Alternatively, the present compounds can be formed into liquid preparations such as solutions, suspensions, emulsions and so on.

For non-oral administration, may be mentioned injection preparations, where the present compounds are combined with water, ethanol, glycerol or the like.

The amount of the compounds (1) according to the present invention or their pharmaceutically acceptable salts required for the treatment or the prevention of a subject suffering from aforementioned diseases differs depending on the physical form of the preparation, administration route, age or conditions of the disease. Generally, the amount via oral route administration for an adult is 1–1000 mg and preferably 5–500 mg per day. It is preferred that the compounds be administered as divided into two to three times a day.

EXAMPLES

The present invention will hereinafter be described in more detail by way of examples, which however, should not be construed as limiting the invention thereto.

First, processes for preparing the intermediates for the present compounds (1) are described in the following Reference Examples 1–3.

Reference Example 1

Preparation of 2-[(4-chlorophenyl)sulfonylaminomethyl]indan:

The title compound was obtained via the following Steps 1 and 2.

Step 1

Preparation of 2-(benzyloxycarbonylaminomethyl)indan:

17.6 g (0.10 mol) of (indan-2-yl)acetic acid was dissolved in 150 ml of toluene, to which were added 15.3 ml (0.11 mol) of triethylamine and 33.0 g (0.12 mol) of diphenylphosphorylazide, and stirred at room temperature for 30 minutes. The mixture was added with 16.6 g (0.15 mol) of benzyl alcohol and refluxed for 18 hours. After cooling, the solvent was distilled under reduced pressure, and the residue was added with 500 ml of ethyl acetate, washed with 1N sodium hydroxide, and condensed. The residue was purified by silica gel column chromatography (ethyl acetate:hexane=1:3), and the crystals collected were recrystallized from a solvent mixture of ethyl acetate and hexane to obtain 24.3 g of 2-(benzyloxycarbonylaminomethyl)indan as colorless needles. Yield: 86%

The melting point, IR and MS data are as follows:
Melting point: 87–89° C.
IR(KBr)cm$^{-1}$: 3325, 1675, 1525

MS(m/z): 281 (M+)

Step 2

Preparation of 2-[(4-chlorophenyl)sulfonylaminomethyl]indan:

10.6 g (37.7 mmol) of 2-(benzyloxycarbonylaminomethyl)indan was dissolved in 100 ml of methanol, to which 1.3 g of palladium on carbon was added and stirred for 4 hours in the stream of hydrogen. The catalyst was removed by filtration, the solvent was evaporated, and 5.04 g of 2-(aminomethyl)indan was obtained. The obtained compound was immediately dissolved in 150 ml of methylene chloride, to which 100 ml of water and 6.2 g of potassium carbonate were added, and the mixture was vigorously stirred. 8.02 g (38.0 mmol) of 4-chlorobenzenesulfonyl chloride was added thereto portionwise under ice-cooling, followed by stirring for 30 minutes. The organic phase was collected, dried and the solvent was removed by distillation. The crystalline residue was recrystallized from a solvent mixture of ethyl acetate and hexane to obtain 9.82 g of 2-[(4-chlorophenyl)sulfonylaminomethyl]indan as colorless needles. Yield: 76%

The melting point, IR and MS data are as follows:

Melting point: 134°–135° C.

IR(KBr)cm$^{-1}$: 3250, 1315, 1150

MS(m/z): 321 (M+)

The chemical formula is as follows:

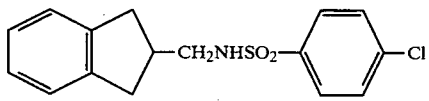

Reference Example 2

Preparation of 2-[3-(4-chlorophenyl)sulfonylaminopropyl]indan:

The above compound was obtained via the following Steps 1 to 5.

Step 1

Preparation of 2-(indan-2-yl)ethanol:

1.02 g (26.8 mmol) of lithium aluminum hydride was suspended in 100 ml of tetrahydrofuran, to which was added dropwise a solution of 10 ml tetrafuran containing 5.06 g (26.6 mmol) of methyl(indan-2-yl)acetate under ice-cooling. After completion of the addition, stirring was continued for 1 hour, during which 1 ml water, 1 ml of 15% sodium hydroxide and 3 ml water were added dropwise in this order for decomposing the excessive reducing agent. The solid matter was removed by filtration, the filtrate was condensed and the residue was purified by silica gel column chromatography (ethyl acetate:hexane=1:4) to obtain 4.30 g of a colorless oil. Yield: 100%

The IR and MS data are as follows:

IR(neat)cm$^{-1}$: 3320, 2920, 1480, 1050

MS(m/z): 162 (M+)

Step 2

Preparation of (indan-2-yl)acetaldehyde:

18.5 g of pyridinium chloromate and 70 g of Celite (No. 545) were suspended in 220 ml of methylene chloride, to which 15 ml solution of methylene chloride containing 4.30 g (26.6 mmol) of ethanol was added dropwise under ice-cooling. Stirring was continued for 1 hour under the ice-cooling condition, and then 2 hours at room temperature. The reaction product was added with 250 ml ether for dilution, and subsequently passed through 100 g of a layered silica gel for separating inorganic matters. The solvent was distilled off to obtain 3.97 g of (indan-2-yl)acetaldehyde as a colorless oil. Yield: 93%

The IR and MS data are as follows:

IR(neat)cm$^{-1}$: 1720, 1615, 1580

MS(m/z): 160 (M+)

Step 3

Preparation of benzyl-4-(indan-2-yl)-2-butenoate:

3.97 g (24.8 mmol) of (indan-2-yl)acetaldehyde was dissolved in 50 ml of methylene chloride, to which was added 12.2 g (29.8 mmol) of benzyloxycarbonylmethylene triphenyl phosphorane and stirred for 1.5 hours. The solvent was distilled off and the residue was purified by silica gel column chromatography (ethyl acetate:hexane=1:20) to obtain 6.45 g colorless oil. Yield: 89%

The IR and MS data are as follows:

IR(neat)cm$^{-1}$: 1715, 1650

MS(m/z): 292 (M+)

Step 4

Preparation of 4-(indan-2-yl)butanoic acid:

6.45 g (22.1 mmol) of benzyl-4-(indan-2-yl)-2-butenoate was dissolved in 120 ml of methanol, to which 0.6 g of 10% palladium on carbon was added and stirred vigorously for 2.5 hours in the stream of hydrogen. The catalyst was removed by filtration, the filtrate was condensed to obtain 3.84 g of crystalline 4-(indan-2-yl)butanoic acid. Yield: 85%

The melting point and MS data are as follows:

Melting point: 75° C.

MS(m/z): 204 (M+)

Step 5

Preparation of 2-[3-(4-chlorophenyl)sulfonylaminopropyl]indan:

The title compound was synthesized in accordance with the procedure of Step 2 of Reference Example 1, and recrystallized from a solvent mixture of ethyl acetate and hexane. Yield: 68%

The melting point, IR and MS data are as follows:

Melting point: 103°–104° C.

IR(nujol)cm$^{-1}$: 3250, 1615, 1575

MS(m/z): 349 (M+)

The chemical formula is as follows:

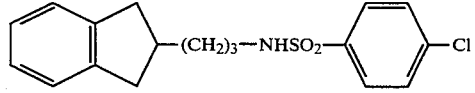

Reference Example 3

Preparation of 2-[2-(4-chlorophenyl)sulfonylaminoethyl]indan:

The title compound was obtained via the following Steps 1 to 3.

Step 1

Preparation of (indan-2-yl)acetamide:

35.3 g (0.20 mol) of (indan-2-yl)acetic acid was dissolved in 350 ml methylene chloride, to which was added 26.5 g (0.22 mol) of thionyl chloride and stirred for 4 hours at room temperature, followed by refluxing for further 1.5 hours. After cooled and condensed under reduced pressure, the obtained oily residue was dissolved in 100 ml ethyl acetate and added dropwise to 200 ml conc. aqueous ammonia while stirred vigorously under ice-cooling. After stirring for 20 minutes, the precipitates were collected by filtration and recrystallized from a solvent mixture of ethyl acetate and ethanol. 32.1 g of colorless crystal was obtained. Yield: 95%

The melting point, IR and MS data are as follows:
Melting point: 152°–154° C.
IR(KBr)cm$^{-1}$: 3340, 3160, 1665, 1625
Ms(m/z): 175 (M+)

Step 2

Preparation of 2-(indan-2-yl)ethylamine:

8.77 g (0.23 mol) of lithium aluminum hydride was suspended in 400 ml of tetrahydrofuran, to which was added a suspension of 100 ml tetrahydrofuran containing 27.8 g (0.160 mol) of (indan-2-yl)acetamide under ice-cooling. The mixture was stirred for 30 minutes at room temperature, then refluxed for 5 hours. Under ice-cooling, 9 ml of water, 9 ml of 15% sodium hydroxide and 26 ml water were added thereto dropwise in this order for decomposing the excessive reagent and separating the solid matter. The filtrate was condensed to obtain 26.1 g of an oily material. Yield: 100%

The IR and MS data are as follows:
IR(neat)cm$^{-1}$: 3360, 3280, 1600, 1585
MS(m/z): 161 (M+)

Step 3

Preparation of 2-[2-(4-chlorophenyl)sulfonylaminoethyl]indan:

The Step 2 of Reference Example 1 was followed and recrystallization was carried out from a solvent mixture of ethyl acetate and isopropylether. Yield: 83%

The melting point, IR and MS data are as follows:
Melting point: 118°–121° C.
IR(KBr)cm$^{-1}$: 3300, 1320, 1155
MS(m/z): 335 (M+)

The chemical formula is as follows:

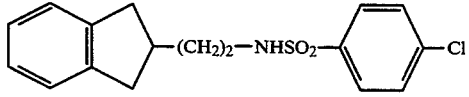

Reference Example 4

Preparation of 2-[4-(4-chlorophenyl)sulfonylaminobutyl]indan:

The process of Reference Example 3 was followed starting 4-(indan-2-yl)butanoic acid to obtain the title compound.

The melting point, IR and MS data are as follows:
Melting point: 77° C.
IR(KBr)cm$^{-1}$: 3260, 1150
MS(m/z): 363 (M+)

The chemical formula is as follows:

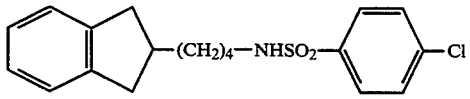

EXAMPLE 1

Preparation of [2-(phenylsulfonylaminomethyl)indan-5-yl]acetic acid:

The aforementioned process D was followed to obtain the title compound via Steps 1 to 4.

Step 1

Preparation of [5-(ethoxycarbonylmethyl)indan-2-yl]acetic acid:

17.6 g (0.10 mol) of(indan-2-yl)acetic acid and 16.9 g (0.10 mol) of ethyl-alpha-chloro-alpha-(methylthio)acetate were dissolved in 100 ml of dichloroethane, to which 17.6 ml (0.15 mol) of stannic chloride was added dropwise under ice-cooling. The mixture was stirred for 40 minutes at room temperature, the reaction mixture was poured into ice-water, and the organic phase was washed with water, dried and condensed. The residue was dissolved in 250 ml acetic acid, and added with 70 g of zinc powder and heated at 110° C. for 1 hour. After cooling, the solid matter was separated by filtration, and the filtrate was condensed under reduced pressure. The residue was added with 500 ml of chloroform, washed with water and dried. The solvent was then distilled off under reduced pressure to obtain 24.1 g of colorless solid. Yield: 92%

The melting point, IR and MS data are as follows:
Melting point: 56°–57° C.
IR(KBr)cm$^{-1}$: 2990, 2910, 1725, 1680
MS(m/z): 262 (M+)

Step 2

Preparation of Ethyl[2-(benzyloxycarbonylaminomethyl)-indan-5-yl]acetate:

11.2 g (42.8 mmol) of [5-(ethoxycarbonylmethyl)indan-2-yl]acetic acid and 6.5 ml (46.7 mmol) triethylamine were dissolved in 140 ml of toluene, to which was added 14.1 g (51.4 mmol) of diphenylphosphorylazide, followed by stirring for 30 minutes at room temperature. Subsequently, 5.05 g (46.7 mmol) of benzyl alcohol was added and refluxed for 14 hours. After cooling, the reaction mixture was washed with 1N hydrochloric acid, water, 1N sodium hydroxide and water in this order and dried. The solvent was distilled off and the residue was purified by silica gel column chromatography (chloroform) to obtain 12.7 g colorless solid. Yield: 81%

The melting point, IR and MS data are as follows:
Melting point: 38°–41° C.
IR(KBr)cm$^{-1}$: 1725, 1675
MS(m/z): 367 (M+)

Step 3

Preparation of ethyl[2-phenylsulfonylaminomethyl)indan-5-yl]acetate:

1.80 g (4.90 mmol) of ethyl[2-carbobenzyloxycarbonylaminomethyl)indan-5-yl]acetate was dissolved in 30 ml of methanol, to which 500 mg of 10% palladium on carbon was added and stirred for 2 hours in the stream of hydrogen. The catalyst was removed by filtration, the filtrate was condensed and the residue was dissolved in 15 ml of ethyl acetate. 10 ml of water and 1.18 g (8.51 mmol) of potassium carbonate was added thereto, and further added dropwise 902 mg (5.11 mmol) of benzenesulfonylchloride. After stirring for 1 hour subsequent to the addition, the organic phase was collected, dried and condensed under reduced pressure. The residue was purified by silica gel column chromatography (chloroform) to obtain 1.78 g of colorless oil. Yield: 97%

The IR and MS data are as follows:
IR(nujol)cm$^{-1}$: 1725, 1615, 1580
MS(m/z): 373 (M+)

Step 4

Preparation of [2-(phenylsulfonylaminomethyl)indan-5-yl]acetic acid:

844 mg (2.26 mmol) of ethyl[2-(phenylsulfonylaminomethyl)-indan-5-yl]acetate was dissolved in 3 ml of methanol, to which was added 5 ml of 1N sodium hydroxide and stirred for 1 hour at room temperature. Methanol was removed and the aqueous phase was washed with chloroform, and added with 1N hydrochloric acid for making the system acidic. The precipitates were extracted with ethyl acetate, dried and condensed. The residue was recrystallized from ethyl acetate to obtain 679 mg crystals. Yield: 87%

The melting point, IR and MS data are as follows:
Melting point: 140°-141° C.
IR(KBr)cm$^{-1}$: 3305, 2950, 1695
MS(m/z): 345 (M+)
The chemical formula is as follows:

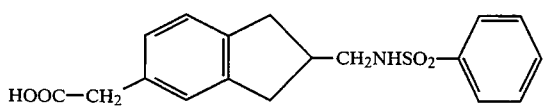

EXAMPLES 2 to 22

The steps in Example 1 above were followed, and compounds having the following nomenclature, chemical formulas, melting points, IR and MS data were obtained.

The terms in the parentheses subsequent to the melting point data indicate solvents from which the compounds were recrystallized.

EXAMPLE 2

[2-[(4-methylphenyl)sulfonylaminomethyl]indan-5-yl]acetic acid:

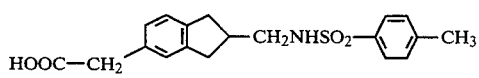

Melting point: 153–156° C. (Ethanol)
IR(KBr)cm$^{-1}$: 3250, 2930, 1715
MS(m/z): 359 (M+)

EXAMPLE 3

[2-[(3,4-dimethoxyphenyl)sulfonylaminomethyl]indan-5-yl]acetic acid:

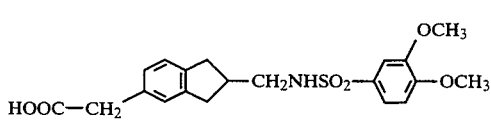

Melting point: 132°-133° C. (Ethanol)
IR(KBr)cm$^{-1}$: 3255, 2930,
MS(m/z): 405 (M+)

EXAMPLE 4

[2-[(trans-2-styryl)sulfonylaminomethyl]indan-5-yl]acetic acid:

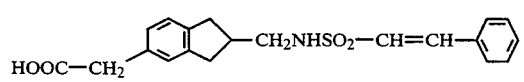

Melting point: 170°-172° C. (Ethanol)
IR(KBr)cm$^{-1}$: 3260, 2930, 1695
MS(m/z): 371 (M+)

EXAMPLE 5

[2-(benzylsulfonylaminomethyl)indan-5-yl]acetic acid:

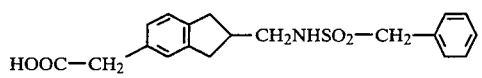

Melting point: 181°-182° C. (Ethanol)
IR(KBr)cm$^{-1}$: 3225, 2930,
MS(m/z): 359 (M+)

EXAMPLE 6

[2-(1-naphthylsulfonylaminomethyl)indan-5-yl]acetic acid:

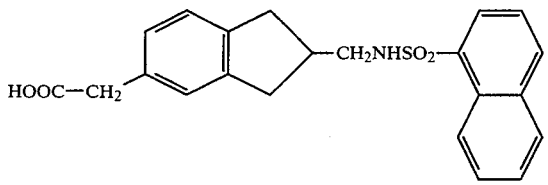

Melting point (decomposed): 58°-60° C.
IR(KBr)cm$^{-1}$: 3275, 2920, 1700
MS(m/z): 395 (M+)

EXAMPLE 7

[2-(2-naphthylsulfonylaminomethyl)indan-5-yl]acetic acid:

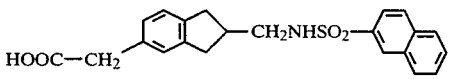

Melting point: 180°-182° C. (Ethanol)
IR (KBr) cm$^{-1}$: 3230, 1925, 1690
MS(m/z): 395 (M+)

EXAMPLE 8

[2-(2-thienylsulfonylaminomethyl)indan-5-yl]acetic acid:

Melting point: 110°-111° C. (aqueous methanol)
IR(KBr)cm$^{-}$: 3250, 2920, 1700
MS(m/z): 351 (M+)

EXAMPLE 9

[2-[(5-phenylsulfonyl-2-thienyl)sulfonylaminomethyl)indan-5-yl]acetic acid:

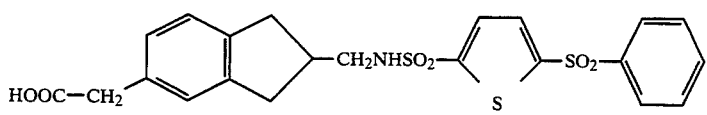

Melting point: 164°–166° C. (Ethanol)
IR(KBr)cm⁻¹: 3260, 2920, 1695
Ms(m/z): 491 (M+)

EXAMPLE 10

[2-[(4-trifluoromethyphenyl)sulfonylaminomethyl)indan-5-yl]acetic acid:

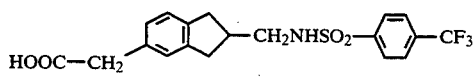

Melting point (decomposed): 183°–186° C. (Ethanol)
IR(KBr)cm⁻¹: 3275, 2950, 1690, 1325, 1150
MS(m/z): 413 (M+)

EXAMPLE 11

[2-[(2,4-dichlorophenyl)sulfonylaminomethyl)indan-5-yl]acetic acid:

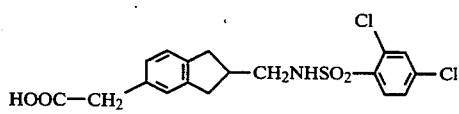

Melting point (decomposed): 153°–154° C. (Ethanol)
IR(KBr)cm⁻¹: 3325, 2945, 1700, 1330, 1165
MS(m/z): 413 (M+)

EXAMPLE 12

2-[(4-methoxyphenyl)sulfonylaminomethyl)indan-5-yl]acetic acid:

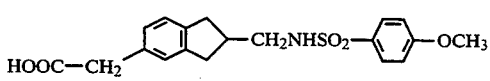

Melting point (decomposed): 171–173° C. (Ethanol)
IR(KBr)cm⁻¹: 3280, 2950, 1695, 1320, 1155
MS(m/z): 375 (M+)

EXAMPLE 13

[2-[(4-fluorophenyl)sulfonylaminomethyl)indan-5-yl]acetic acid:

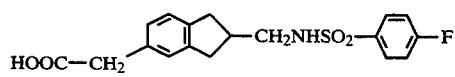

Melting point: 180°–181° C. (aqueous ethanol)
IR(KBr)cm⁻¹: 3300, 1700, 1155
MS(m/z): 363 (M+)

EXAMPLE 14

[2-[(4-bromophenyl)sulfonylaminomethyl)indan-5-yl]acetic acid:

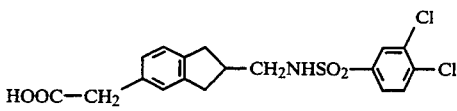

Melting point: 182°–183° C. (aqueous ethanol)
IR(KBr)cm⁻¹: 3295, 2940, 1700, 1330, 1170
MS(m/z): 423(M+)

EXAMPLE 15

[2-[(3,4-dichlorophenyl)sulfonylaminomethyl)indan-5-yl]acetic acid:

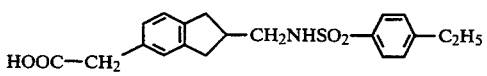

Melting point: 174°–176° C. (aqueous ethanol)
IR(KBr)cm⁻: 3250, 1695, 1325, 1160
MS(m/z): 415 (M+)

EXAMPLE 16

[2-[(4-ethylphenyl)sulfonylaminomethyl)indan-5-yl]acetic acid:

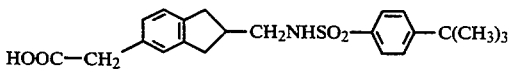

Melting point: 140°–143° C. (Ethyl acetate-hexane)
IR(KBr)cm⁻¹: 3280, 1700, 1155
MS(m/z): 373 (M+)

EXAMPLE 17

[2-[(4-t-butylphenyl)sulfonylaminomethyl)indan-5-yl]acetic acid:

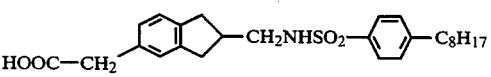

Melting point: 187–189° C. (aqueous ethanol)
IR(KBr)cm⁻¹: 3260, 1700, 1160
MS(m/z): 401 (M+)

EXAMPLE 18

[2-[(4-octylphenyl)sulfonylaminomethyl)indan-5-yl]acetic acid:

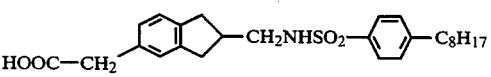

Melting point: 136°–137 ° C. (aqueous ethanol)
IR(KBr)cm⁻¹: 3300, 2920, 1700, 1330, 1155
MS(m/z): 457 (M+)

EXAMPLE 19

2-[(4-trifluoromethoxyphenyl)sulfonylaminomethyl)indan-5-yl]acetic acid:

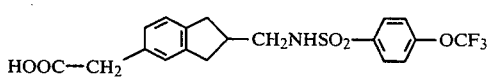

Melting point: 185°–186° C. (aqueous ethanol)
IR(KBr)cm$^{-1}$: 3300, 2940, 1700, 1155
MS(m/z): 429 (M+)

EXAMPLE 20

[2-[(4-butoxyphenyl)sulfonylaminomethyl)indan-5-yl]acetic acid:

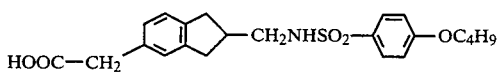

Melting point 151°–152° C. (aqueous ethanol)
IR(KBr)cm$^{-1}$: 3270, 1690
MS(m/z): 417 (M+)

EXAMPLE 21

2-[(4-cyanophenyl)sulfonylaminomethyl)indan-5-yl]acetic acid:

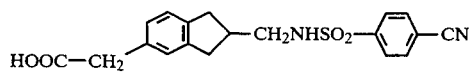

Melting point: 198°–199° C. (aqueous ethanol)
IR(KBr)cm$^{-1}$: 3300, 2940, 1700, 1335, 1160
MS(m/z): 370 (M+)

EXAMPLE 22

[2-[(4-nitrophenyl)sulfonylaminomethyl)indan-5-yl]acetic acid:

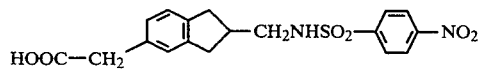

Melting point: 148°–149° C. (aqueous ethanol)
IR(KBr)cm$^{-1}$: 3240, 1705, 1350, 1155
MS(m/z): 390 (M+)

EXAMPLE 23

[2-[(4-aminophenyl)sulfonylaminomethyl)indan-5-yl]acetic acid:

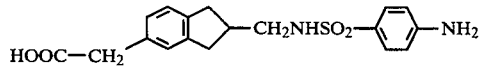

1.95 g of [2-[(4-nitrophenyl)sulfonylaminomethyl)indan-5-yl]acetic acid obtained in Example 22 was dissolved in 50 ml of methanol and added with 200 mg of 10% palladium on carbon, followed by stirring for 2 hours in the stream of hydrogen gas. The catalyst was removed by filtration, the filtrate was condensed and the residue was recrystallized from ethanol to obtain 1.43 g of crystals. Yield: 79%

Melting point: 201°–202° C.

IR(KBr)cm$^{-1}$: 3470, 3380, 3280, 1695, 1150
MS(m/z): 360 (M+)

EXAMPLE 24

Preparation of [2-[(4-chlorophenyl)sulfonylaminomethyl)indan-5-yl]acetic acid:

The procedure of the aforementioned Process D was followed to obtain the title compound via the following Steps 1 to 3.

Step 1

Ethyl [2-[(4-chlorophenyl)sulfonylaminomethyl)indan-5-yl]acetate:

16.1 g (50.0 mmol) of [2-[(4-chlorophenyl)sulfonylaminomethyl)indan and 9.27 g (55.0 mmol) of ethyl alpha-chloro-alpha-(methylthio)acetate were dissolved in 50 ml of methylene chloride, to which 6.44 ml (55.0 mmol) of stannic chloride was slowly added dropwise. After stirring for 3 hours, the reaction mixture was poured into ice-water, and the organic phase was collected, washed, dried and condensed. The residue was dissolved in 180 ml of acetic acid, added with 40 g of zinc powder and heated at 110° C. for 1 hour. After cooling, the precipitates were filtrated and washed thoroughly with chloroform and the solvent was removed. The residue was dissolved in 300 ml of ethyl acetate, and washed with water, saturated aqueous sodium bicarbonate solution and water in this order, and dried. The solvent was distilled off under reduced pressure, and the residue was recrystallized from a solvent mixture of ethyl acetate and hexane to obtain 16.7 g of colorless needles. Yield: 82%.

The melting point, IR and MS data are shown below:
Melting point: 94°–96° C.
IR(KBr)cm$^{-1}$: 3230, 1730
MS(m/z): 379 (M+)

Step 2

Preparation of [2-[(4-chlorophenyl)sulfonylaminomethyl)indan-5-yl]acetic acid:

16.5 g of ethyl [2-[(4-chlorophenyl)sulfonylaminomethyl)indan-5-yl]acetate was suspended in 50 ml of 1N sodium hydroxide, and heated at 80° C. for 1 hour. After cooling, conc. HCl was added thereto to make the system acidic. The precipitates were collected by filtration, followed by recrystallization from 80% ethanol to obtain 14.0 g of colorless needles. Yield: 91%

The melting point, IR and MS data are shown below:
Melting point: 182°–186° C.
IR(KBr)cm$^{-1}$: 3340, 1700
MS(m/z): 379 (M+)

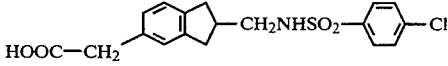

Step 3

Preparation of sodium [2-[(4-chlorophenyl)sulfonylaminomethyl)indan-5-yl]acetate:

2.65 g (7.00 mmol) of [2-[(4-chlorophenyl)sulfonylaminomethyl]indan-5-yl]acetic acid obtained above was dissolved in 15 ml of 1N sodium hydroxide, and passed through 100 ml of polystyrene gel (HP-20). Elution was carried out with 80% methanol, and the eluate was condensed to obtain colorless crystals, followed by recrystallization from 95% ethanol to obtain 2.39 g of colorless prisms. Yield: 85%

The melting point is as follows:
Melting point (decomposed): 133°–135° C.

The chemical formula is as follows:

EXAMPLES 25-28

The steps in Example 24 above were followed, and compounds having the following nomenclature, chemical formulas, melting points, IR and MS data were obtained.

EXAMPLE 25

[2-(2-phenylsulfonylaminoethyl)indan-5-yl]acetic acid:

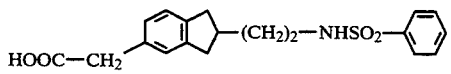

Melting point: 102°-103° C. (Ethyl acetate—hexane)
IR(nujol)cm$^{-1}$: 3240, 1695
MS(m/z): 359 (M+)

EXAMPLE 26

[2-[2-(4-chlorophenyl)sulfonylaminoethyl]indan-5-yl]acetic acid:

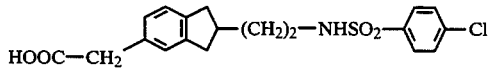

Melting point: 146°-147° C. (Ethyl acetate—hexane)
IR(nujol)cm$^{-1}$: 3330, 1705
MS(m/z): 393 (M+)

EXAMPLE 27

[2-[3-(4-chlorophenyl)sulfonylaminopropyl]indan-5-yl]acetic acid:

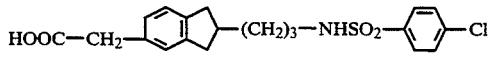

Melting point: 163°-164° C. (aqueous ethanol)
IR(KBr)cm$^{-1}$: 3260, 1690
MS(m/z): 407 (M+)

EXAMPLE 28

[2-[4-(4-chlorophenyl)sulfonylaminobutyl]indan-5-yl]acetic acid:

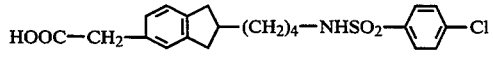

Melting point: 126° C. (aqueous ethanol)
IR(KBr)cm$^{-1}$: 3280, 1700
MS(m/z): 421 (M+)

EXAMPLE 29

Preparation of 2-(phenylsulfonylaminomethyl)indan-5-hydroxyacetic acid:

The aforementioned Process B was followed to obtain the above compound via the following steps 1 to 8.
Step 1
Preparation of methyl(5-acetylindan-2-yl)acetate:

160 ml of methylene chloride was added with 52.9 g (0.388 mol) of anhydrous aluminum chloride, and further added with 40 ml of methylene chloride containing 25.03 g (0.132 mol) of methyl(indan-2-yl)acetate under ice-cooling. Subsequently, 13.1 ml (0.185 mol) of acetyl chloride was added thereto dropwise. Stirring was conducted for 40 minutes at the same temperature. The reaction mixture was poured into ice-water and the organic phase was collected. After washing and drying, the solvent was condensed under reduced pressure, and the residue was purified by silica gel column chromatography (ethyl acetate:hexane=1:2) to obtain 27.8 g of an oily product. Yield: 91%

The IR and MS data are as follows:
IR(neat)cm$^{-1}$: 1725, 1690
MS(m/z): 232 (M+)
Step 2
Methyl(5-acetoxyindan-2-yl)acetate:

11.0 g (47.0 mmol) of methyl(5-acetylindan-2-yl)acetate was dissolved in 200 ml of methylene chloride, to which was added 14.6 g (67 mmol) of m-chloroperbenzoic acid and stirred for 4 hours at room temperature, followed by refluxing for 17 hours. The reaction mixture was washed with saturated aqueous sodium bicarbonate and water in this order, dried and then the solvent was removed. The residue was purified by silica gel column chromatography (chloroform) to obtain 11.3 g of an oily product. Yield: 97%

IR and MS data are as follows:
IR(neat)cm$^{-1}$: 1750, 1730
MS(m/z): 248 (M+)
Step 3
Preparation of (5-benzyloxyindan-2-yl)acetic acid:

9.62 g (38.8 mmol) of methyl(5-acetoxyindan-2-yl)acetate was dissolved in 150 ml of methanol, to which was added 1.17 g (8.5 mmol) of potassium carbonate and stirred for 1 hour at room temperature. The solvent was distilled off under reduced pressure, and the residue was dissolved in 150 ml of acetone. 5.98 g (43.0 mmol) of potassium carbonate, 7.27 g (42.5 mmol) of benzylbromide were added thereto and refluxed for 5 hours. After cooling, the precipitates were filtrated and condensed under reduced pressure. The residue was dissolved in 100 ml of methanol, to which 12 ml of 20% sodium hydroxide were added and the mixture was heated at 50° C. for 1 hour. After cooling, methanol was removed, the residue was made acidic with conc. HCl, and the precipitates were extracted with chloroform. The organic phase was washed with water, dried and condensed under reduced pressure to obtain a pale brown solid. Recrystallization was carried out from a solvent mixture of isopropylether and ethyl acetate to obtain 5.97 g of colorless crystals. Yield: 68%

The melting point and IR and MS data are as follows:
Melting point: 127°-129° C.
IR(neat)cm$^{-1}$: 1695, 1615, 1485
MS(m/z): 282 (M+)
Step 4
Preparation of 5-benzyloxy-2-(t-butoxycarbonylaminomethyl)indan:

4.27 g (15.0 mmol) of (5-benzyloxy-2-yl)acetic acid was dissolved in 120 ml of t-butanol, to which were added 1.96 (19.4 mmol) of triethylamine and 5.03 g (18.3 mmol) of diphenylphosphorylazide in this order, and the mixture was refluxed for 27 hours. After cooling, the reaction mixture was condensed under reduced pressure, the residue was dissolved in 200 ml of ethyl acetate, followed by washing with 1N hydrochloric acid, water, 1N sodium hydroxide and water in this order, and then the solvent was removed. The residue was purified by silica gel column chromatography (chloroform) and recrystallized from ethyl acetate and isopropylether to obtain 4.71 g of colorless crystals. Yield: 89%

The melting point, IR and MS data are as follows:
Melting point: 95–98° C.
IR(KBr)cm$^{-1}$: 3350, 1670
MS(m/z): 353 (M+)

Step 5

Preparation of 2-(t-butoxycarbonylaminomethyl)-5-hydroxyindan:

3.53 g (10.0 mmol) of 5-benzyloxy-2-(t-butoxycarbonylaminomethyl)indan was dissolved in 100 ml of methanol and added with 0.3 g of 10% palladium on carbon, followed by stirring for 4 hours in the stream of hydrogen gas. The catalyst was removed by filtration, and the filtrate was condensed under reduced pressure. The residue was purified by silica gel column chromatography (ethyl acetate: hexane=1:2) to obtain 2.79 g of a colorless oil. Yield: 94%

The IR and MS data are as follows:
IR(neat)cm$^{-1}$: 3350, 1690
MS(m/z): 263 (M+)

Step 6

Preparation of ethyl[2-(t-butoxycarbonylaminomethyl)indan-5-oxy]acetate:

1.85 g (6.20 mmol) of 2-(t-butoxycarbonylaminomethyl)5-hydroxyindan was dissolved in 20 ml of acetone, to which were added 1.52 g (11.0 mmol) of potassium carbonate and 1.10 g (6.60 mmol) of ethyl bromoacetate, and refluxed for 3.5 hours. After cooling, the precipitates were filtrated, and the residue obtained by condensing the filtrate was purified by silica gel column chromatography (ethyl acetate:hexane=1:2) to obtain 1.90 g of colorless crystals. Yield: 80%

The melting point, IR and MS data are shown below:
Melting point: 56°–63° C.
IR(neat)cm$^{-1}$: 1730, 1675
MS(m/z): 343 (M+)

Step 7

Preparation of ethyl[2-(phenylsulphonylaminomethyl)indan-5-oxy]acetate:

1.77 g (5.00 mmol) of ethyl[2-(t-butoxycarbonylaminomethyl)-indan-5-oxy]acetate was dissolved in 6 ml of methylene chloride, to which was added 4 ml of trifluoroacetic acid under ice-cooling and stirred for 1 hour. The reaction mixture was diluted with 40 ml of methylene chloride. A solution of 40 ml water containing 8.37 g (60 mmol) of potassium carbonate was added thereto and stirred vigorously. 10 minutes after, 1.07 g (6.00 mmol) of phenylsulfonylchloride was added thereto, and stirred for further 1.5 hours. The organic phase was collected, dried and condensed, and the residue was purified by column gel chromatography (ethyl acetate:hexane=1:1) to obtain 1.68 g of a colorless oil. Yield: 88%

The IR and MS data are shown below:
IR(nujol)cm$^{-1}$: 3280, 1750, 1320, 1155
MS(m/z): 389 (M+)

Step 8

Preparation of 2-(phenylsulphonylaminomethyl)indan-5-hydroxy acetic acid:=

1.67 g (4.36 mmol) of ethyl[2-(phenylsulphonylaminomethyl)indan-5-oxy]acetate was dissolved in a mixture of 30 ml methanol and 6 ml of 1N sodium hydroxide, and stirred for 1 hour at room temperature. Methanol was removed, the residue was made acidic by conc. HCl, and the precipitates were extracted with chloroform. After condensation, the solid matter was recrystallized from acetic acid and isopropylether to obtain 1.33 g of colorless crystals. Yield: 86%

The melting point, IR and MS data are shown below:
Melting point: 150°–151° C.
IR(KBr)cm$^{-1}$: 3270, 1745
MS(m/z): 361 (M+)

The chemical formula is as follows:

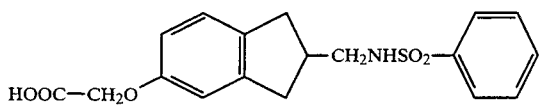

EXAMPLES 30–32

The steps in Example 29 above were followed, and compounds having the following nomenclature, chemical formulas, melting points, IR and MS data were obtained.

EXAMPLE 30

2-[(4-chlorophenyl)sulfonylaminomethyl)indan-5-hydroxyacetic acid:

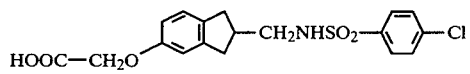

Melting point (decomposed): 185°–188° C. (aqueous ethanol)
IR(KBr)cm$^{-1}$: 3240, 1720
MS(m/z): 395 (M+)

EXAMPLE 31

2-[(4-methoxyphenyl)sulfonylaminomethyl)indan-5-hydroxy acetic acid:

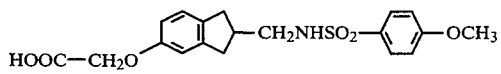

Melting point: 155°–156° C. (aqueous ethanol)
IR(KBr)cm$^{-1}$: 3270, 1750, 1730, 1705
MS(m/z): 391 (M+)

EXAMPLE 32

2-[2-(4-chlorophenyl)sulfonylaminoethyl)indan-5-hydroxy acetic acid:

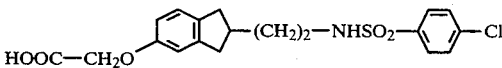

Melting point: 156°–158° C. (aqueous ethanol)
IR(KBr)cm$^{-1}$: 3330, 1715
Ms(m/z): 409 (M+)

EXAMPLE 33

Preparation of [2-[(4-chlorophenyl)sulfonylaminomethyl]-indan-5-yl]carboxylic acid:

The aforementioned Process C was followed to obtain the title compound via the following Steps 1 to 2.

Step 1

Preparation of 5-acetyl-2-[(4-chlorophenyl)sulfonylaminomethyl]indan:

369 mg (1.15 mmol) of 2-[(4-chlorophenyl)sulfonylaminomethyl)indan was dissolved in 5 ml of methylene chloride, to which were added 460 mg (4.20 mmol) of anhydrous aluminum chloride under ice-cooling and then 302 mg (3.80 mmol) of acetyl chloride dropwise. After stirring for 30 minutes at the same temperature, the reaction solution was admixed with ice, and the organic phase was washed with water and saturated-aqueous sodium bicarbonate, dried and the solvent was removed. The residue was recrystallized from a solvent mixture of ethyl acetate and isopropylether to obtain 310 mg of colorless crystals. Yield: 75%

The melting point, IR and MS data are shown below:
Melting point: 102°–105° C.
IR(KBr)cm⁻: 3250, 1675, 1320, 1150
MS(m/z): 363(M+)
Step 2
Preparation of [2-[(4-chlorophenyl)sulfonylaminomethyl]-indan-5-yl]carboxylic acid:

Under ice-salt cooling, 4.90 g (122 mmol) of sodium hydroxide was dissolved in 50 ml of water, to which 1.6 ml (31.0 mmol) of bromine was added dropwise. This mixture was added to a solution of 100 ml of 90% dioxane containing 2.85 g (7.50 mmol) of 5-acetyl-2-[(4-chlorophenyl)sulfonylaminomethyl]indan under cooling in an ice-salt bath. Thereafter, stirring was conducted for 1 hour during which the temperature of the mixture was elevated to room temperature. The reaction solution was added with 10% sodium thiosulfate, and made acidic with 1N HCl, followed by extracting with ethyl acetate. The solvent was removed, and the residue was recrystallized from acetic acid to obtain 2.36 g of colorless crystals. Yield: 86%

The melting point, IR and MS data are shown below:
Melting point (decomposed): 226°–228° C.
IR(KBr)cm⁻¹: 3240, 1675
MS(m/z): 365 (M+)
The chemical formula is as follows:

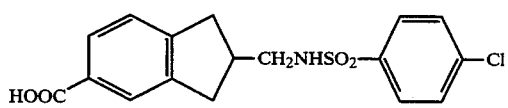

EXAMPLES 34–36

The steps in Example 33 above were followed, and compounds having the following nomenclature, chemical formulas, melting points, IR and MS data were obtained.

EXAMPLE 34

[2-[2-(4-chlorophenyl)sulfonylaminoethyl)indan-5-yl]-carboxylic acid:

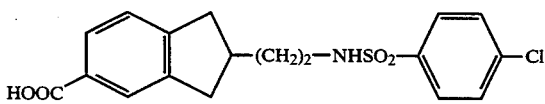

Melting point (decomposed): 210°–213° C.
IR(KBr)cm⁻¹: 3270, 1685
MS(m/z): 379 (M+)

EXAMPLE 35

[2-[3-(4-chlorophenyl)sulfonylaminopropyl)indan-5-yl]carboxylic acid:

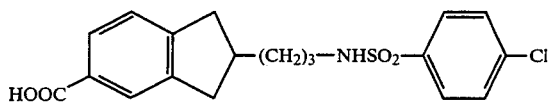

Melting point (decomposed): 183°–186° C.
IR (KBr) cm⁻¹: 3270, 1670
MS(m/z): 393 (M+)

EXAMPLE 36

[2-[4-(4-chlorophenyl)sulfonylaminobutyl)indan-5-yl]carboxylic acid:

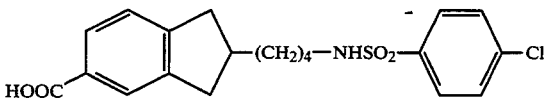

Melting point: 152°–154° C.
IR(KBr)cm⁻¹: 3280, 1685
MS(m/z): 407 (M+)

EXAMPLE 37

Preparation of trans-3-[2-[(4-chlorophenyl)sulfonylaminomethyl)indan-5-yl]acrylic acid:

The aforementioned Process F was followed to obtain the title compound via the following Steps 1 to 3.
Step 1
Preparation of 5-formyl-2[(4-chlorophenyl)sulfonylaminomethyl]indan:

5.33 g (40.0 mmol) of anhydrous aluminum chloride was suspended in 20 ml of methylenechloride and added with 1.61 g (5.00 mmol) of 2-[(4-chlorophenyl)sulfonylaminomethyl]indan, followed by cooling at −20° C. 10 ml of methylene chloride containing as dissolved 0.68 ml (7.5 mmol) of dichloromethylmethylether was slowly added dropwise thereto, followed by stirring for 1 hour at the same temperature. The reaction solution was poured into ice-water and stirred for 1 hour. Thereafter, the organic phase was collected, washed, dried, and the solvent was removed. The residue was purified by silica gel column chromatography (chloroform), followed by recrystallizing from a solvent mixture of ethylacetate and hexane to obtain 375 mg of colorless crystals. Yield: 22%

The melting point, IR and MS data are shown below:
Melting point: 80°–82° C.
IR(KBr)cm⁻¹: 3240, 1685
MS(m/z): 349 (M+)
Step 2
Preparation of ethyl-trans-3-[2-[(4chlorophenyl)sulfonylaminomethyl]indan-5-yl]acrylate:

To 20 ml of methylene chloride, 1.29 g (3.68 mmol) of 5-formyl-2-[( 4-chlorophenyl)sulfonylaminomethyl]indan and 1.28 g (3.68 mmol) of carboethoxymethylene triphenylphosphoran were added and stirred for 16 hours at room temperature. The reaction solution was purified by silica gel column chromatography.(-chloroform), and the precipitates obtained were recrystallized from a solvent mixture of ethyl acetate and hexane. 1.18 g of colorless crystals were obtained. Yield: 77%

The melting point, IR and MS-data are as follows:
Melting point: 113°–115° C.
IR(KBr)cm⁻¹: 3230, 1705, 1630
MS(m/z): 387 (M+)

Step 3

Preparation of trans-3-[2-[(4-chlorophenyl)sulfonylaminomethyl]indan-5-yl]acrylic acid:

465 mg (1.20 mmol) of ethyl-trans-3-[2-[(4-chlorophenyl)sulfonyl-aminoethyl]indan-5-yl]acrylate was suspended in 5 ml of sodium hydroxide and stirred for 5 hours at room temperature. 2N hydrochloric acid was added thereto for making the system acidic, and the precipitated crystals were extracted with methylene chloride. After dried, the solvent was removed, and the residue was recrystallized from ethanol to obtain 405 mg of colorless crystals. Yield: 86%

The melting point, IR and MS data are as follows:
Melting point: 240°–241° C.
IR(KBr)cm$^{-1}$: 3260, 1685, 1630
MS(m/z): 359 (M+)
The chemical formula is as follows:

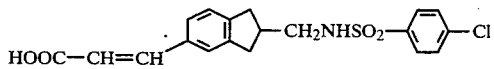

EXAMPLE 38

Preparation of 3-[2-[(4-chlorophenyl)sulfonylaminomethyl]indan-5-yl]propionic acid:

The aforementioned Process F was followed to obtain the title compound via the following Steps 1 to 2.

Step 1

Preparation of ethyl-3-[2-[(4-chlorophenyl)sulfonylaminomethyl]indan-5-yl]propionate:

387 mg (1.00 mmol) of ethyl-trans-3-[2-[(4chlorophenyl)sulfonylaminomethyl]indan-5-yl]acrylate was dissolved in 10 ml of ethanol, to which was added 24 mg (0.1 mmol) of nickel chloride·6H$_2$O. Under ice-cooling, to this solution was added 76 mg (2.00 mmol) of sodium borohydride, followed by stirring at room temperature overnight. The ethanol was distilled off, the residue was added with 10 ml of water, and the obtained product was extracted with ethyl acetate, followed by washing and drying then condensing. The obtained crystals were recrystallized from a solvent mixture of hexane and ether to obtain 241 mg colorless crystals. Yield: 62%

The melting point, IR and MS data are as follows:
Melting point: 90°–93° C.
IR(KBr)cm$^{-1}$: 3260, 1725, 1585, 1320, 1155
MS(m/z): 389 (M+)

Step 2

Preparation of 3-[2-[(4-chlorophenyl)sulfonylaminomethyl]indan-5-yl]propionic acid:

195 mg (0.50 mmol) of ethyl-3-[2-[(4chlorophenyl)-sulfonylaminomethyl]indan-5-yl]propionate was suspended in 3 ml of 2N sodium hydroxide and heated at 70° C. for 2 hours. After cooling, the system was made acidic with conc. HCl in an ice bath. The precipitated crystals were collected, recrystallized from a solvent mixture of ethyl acetate and hexane to obtain 137 mg of colorless flakes. Yield: 76%

The melting point, IR and MS data are as follows:
Melting point: 189°–191° C.
IR(KBr)cm$^{-1}$: 3270, 1695, 1595, 1320, 1160
MS(m/z): 361 (M+)
The chemical formula is as follows:

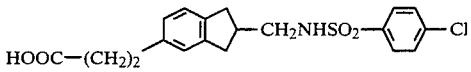

EXAMPLE 39

The steps in Example 38 above were followed, and compounds having the following nomenclature, chemical formulas, melting points, IR and MS data were obtained. Yield: 66%

3-[2-[(4-methoxyphenyl)sulfonylaminomethyl)indan-5-yl]propionic acid:

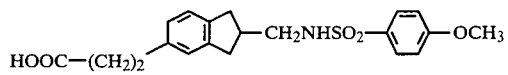

Melting point:. 147°–151° C. (aqueous ethanol)
IR(KBr)cm$^{-1}$: 3260, 1695, 1155
MS(m/z): 389 (M+)

EXAMPLE 40

Preparation of 4-[2-[(4-chlorophenyl)sulfonylaminomethyl]indan-5-yl-4-oxobutanoic acid:

The aforementioned Process E was followed to obtain the title compound via the following Step.

6.82 g (51.2 mmol) of anhydrous aluminum chloride was suspended in 35 ml of dichloroethane, to which was added 4.26 g (13.3 mmol) of 2-[(4-chlorophenyl)sulfonylaminomethyl]indan prepared in Reference Example 1. 2.07 g (20.6 mmol) of succinic anhydride was added portionwise to the mixture under ice-cooling. Thereafter, stirring was carried out for 1.5 hours at room temperature, the reaction solution was poured into ice-water, and then the precipitated crystals were filtrated, washed, and recrystallized to obtain 4.75 g of colorless crystals. Yield: 85%

The melting point, IR and MS data are as follows:
Melting point (decomposed): 192°–194° C.
IR(KBr)cm$^{-1}$: 3250, 1690, 1675
MS(m/z): 421 (M+)
The chemical formula is as follows:

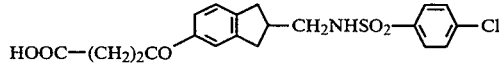

EXAMPLES 41–44:

The procedure in Example 40 above was followed, and compounds having the following nomenclature, chemical formulas, melting points, IR and MS data were obtained.

EXAMPLE 41

4-[2-[2-(4-chlorophenyl)sulfonylaminoethyl)indan-5-yl]-4-oxobutanoic acid:

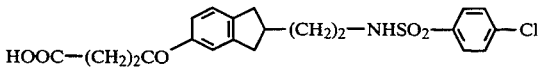

Melting point: 144°–146° C. (acetic aid)
IR(KBr)cm$^{-1}$: 3300, 1715, 1675
MS(m/z): 435 (M+)

EXAMPLE 42

4-[2-[(4-methoxyphenyl)sulfonylaminomethyl)indan-5-yl]-4-oxobutanoic acid:

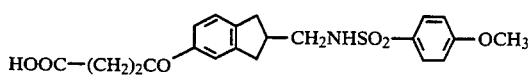

Melting point: 150°-151° C. (aqueous ethanol)
IR(KBr)cm$^{-1}$: 3260, 1695,
MS(m/z): 417 (M+)

EXAMPLE 43

5-[2-[(4-chlorophenyl)sulfonylaminomethyl)indan-5-yl]-4-oxopentanoic acid:

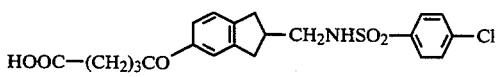

Melting point: 159°-161° C. (Ethanol)
IR(KBr)cm$^{-1}$: 3260, 1690, 1680, 1155
MS(m/z): 435 (M+)

EXAMPLE 44

6-[2-[(4-chlorophenyl)sulfonylaminomethyl)indan-5-yl]-6-oxohexanoic acid:

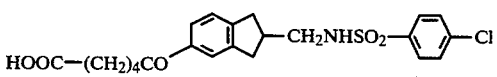

Melting point: 154°-155° C. (aqueous alcohol)
IR(KBr)cm$^{-1}$: 3260, 1680, 1430, 1325, 1155
Ms(m/z): 449 (M+)

EXAMPLE 45

Preparation of 6-[2-[(4-chlorophenyl)sulfonylaminoethyl)indan-5-yl]-3-oxo-2,3,4,5-tetrahydropyridazine:

The title compound was obtained by the following procedure.

1.730 g of 4-[2-[(4-chlorophenyl)sulfonylaminomethyl]indan-5-yl-4-oxobutanoic acid obtained in Example 40 was suspended in acetic acid (12 ml), and added with hydrazine·H$_2$O (332 mg) then refluxed. After 3.5 hours, acetic acid was distilled off under reduced pressure, and the obtained residue was added with saturated aqueous sodium bicarbonate. The crystals produced were collected by filtration. The crystals were recrystallized from acetic acid to obtain 1.331 g of colorless crystals. Yield: 78%

The melting point, IR and MS data are shown below.
Melting point: 193°-194° C.
IR(KBr)cm$^{-1}$: 3250, 1685, 1315, 1150
MS(m/z): 417 (M+)
The chemical formula is as follows:

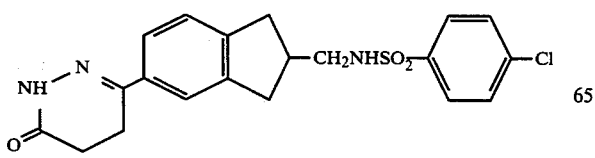

EXAMPLE 46

Preparation of 5-[2-[(4-chlorophenyl)sulfonylaminomethyl]indan-5-yl]-3-oxo-2,3,4-trihydropirazole:

The title compound was obtained via the following steps 1 to 2.

Step 1

Preparation of ethyl 3-[2-[(4chlorophenyl)sulfonylaminomethyl]indan-5-yl]-3-oxopropionate:

The title compound was obtained in a similar procedure to Example 40. Yield: 70%

The melting point, IR and MS data are shown below.
Melting point: 78°-79° C. (Ethyl acetate—isopropyl alcohol)
IR(KBr)cm$^{-1}$: 3240, 2920, 1730, 1675, 1150
MS(m/z): 435 (M+)

Step 2

Preparation of 5-[2-[(4-chlorophenyl)sulfonylaminomethyl]indan-5-yl]-3-oxo-2,3,4-trihydropyrazole:

The title compound was obtained in a similar procedure to Example 45. Yield: 72%

The melting point, IR and MS data are shown below.
Melting point: 274°-275° C. (Acetic acid)
IR(KBr)cm$^{-1}$: 3250, 1700, 1600, 1150
MS(m/z): 403 (M+)
The chemical formula is as follows:

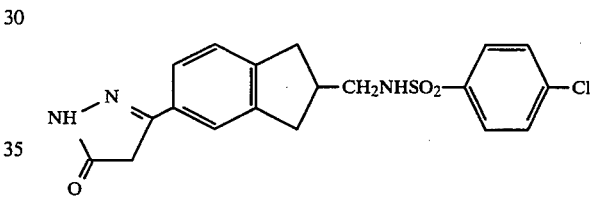

EXAMPLE 47

Preparation of 3-[2-[(4-chlorophenyl)sulfonylaminomethyl]indan-5-yl]-3-hydroxypropionic acid:

The title compound was obtained via the following steps 1 and 2.

Step 1

Preparation of ethyl 3-[2-[(4-chlorophenyl)sulfonylaminomethyl]indan-5-yl]-3-hydroxypropionate:

4.46 g of ethyl 3-[2-[(4-chlorophenyl)sulfonylaminomethyl]indan-5-yl]-3-oxopropionate obtained in Step 1 of Example 46 was dissolved in 60 ml of ethanol, to which 193 mg of sodium borohydride was added under ice-cooling, followed by stirring for 2 hours at the same temperature. Subsequently, the solvent was distilled off under reduced pressure. The residue was added with ethyl acetate, washed with water and dried. The solvent was removed under reduced pressure. The residue was recrystallized from a solvent mixture of ethyl acetate and isopropyl ether to obtain 4.37 g of colorless crystals. Yield: 99%

The melting point, IR and MS data are as follows:
Melting point: 108°-111° C.
IR(KBr)cm$^{-1}$: 3260, 1725, 1325, 1155
MS(m/z): 437 (M+)

Step 2

Preparation of ethyl 3-[2-[(4-chlorophenyl)sulfonylaminomethyl]indan-5-yl]-3-hydroxypropionic acid:

The title compound was obtained by following the procedure similar to Step 4 in Example 1. Yield: 89%

The melting point, IR and MS data are as follows:
Melting point: 173°–174° C. (Ethyl acetate)
IR(KBr)cm$^{-1}$: 3260, 1705, 1325, 1155
MS(m/z): 409 (M+)

The chemical formula is as follows:

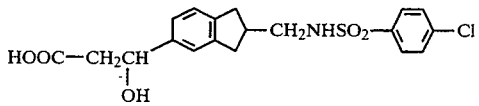

EXAMPLE 48

Preparation of 4-[2-[(4-chlorophenyl)sulfonylaminomethyl]indan-5-yl]butanoic acid:

The title compound was obtained via the following steps 1 and 2.

Step 1

Preparation of ethyl 4-[2-[(4-chlorophenyl)sulfonylaminomethyl]indan-5-yl]-4-oxobutylate:

The title compound was obtained by following the procedure similar to Example 40. Yield 84%

The melting point, IR and MS data are as follows:
Melting point: 86°–87° C. (Ethyl acetate—isopropyl ether)
IR(KBr)cm$^{-1}$: 3240, 1725, 1665, 1160
MS(m/z): 449 (M+)

Step 2

Preparation of ethyl 4-[2-[(4-chlorophenyl)sulfonylaminomethyl]indan-5-yl]butylate:

6.75 g of ethyl 4-[2-[(4-chlorophenyl)sulfonylaminomethyl]indan-5-yl]-4-oxobutylate was dissolved in 10 ml of trifluoroacetic acid; to which 5.4 ml of triethylsilane was added and stirred overnight at room temperature. The reaction solution was added with water, then the product was extracted with ethyl acetate, followed by washing with water, saturated aqueous sodium bicarbonate and saturated saline in this order, drying and distilling off the solvent under reduce pressure. The obtained crystals were recrystallized from a solvent mixture of ethyl acetate and hexane. 5.83 g of colorless crystals were obtained. Yield: 89%

The melting point, IR and MS data are as follows:
Melting point: 70°–71° C.
IR(KBr)cm$^{-1}$: 3260, 1735, 1155
MS(m/z): 435(M+)

The chemical formula is as follows:

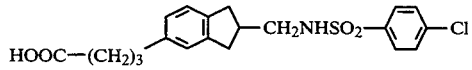

EXAMPLES 49–52

The steps in Example 24 above were followed, and compounds having the following nomenclature, chemical formulas, melting points, IR and MS data were obtained.

EXAMPLE 49

5-[2-[(4-chlorophenyl)sulfonylaminomethyl)indan-5-yl]pentanoic acid:

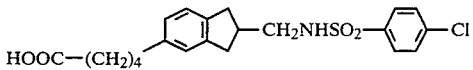

Melting point: 164°–165° C. (Ethanol)
IR(KBr)cm$^{-1}$: 3260, 1700, 1155
MS(m/z): 421 (M+)

EXAMPLE 50

4-[2-[(4-methoxyphenyl)sulfonylaminomethyl)indan-5-yl]butanoic acid:

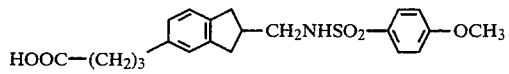

Melting point: 114°–115° C. (aqueous ethanol)
IR(KBr)cm$^{-1}$: 3300, 1700,
MS(m/z): 403 (M+)

EXAMPLE 51

6-[2-[(4-chlorophenyl)sulfonylaminomethyl)indan-5-yl]hexanoic acid:

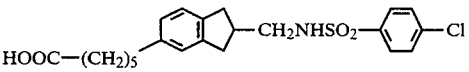

Melting point: 152°–153° C. (aqueous ethanol)
IR(KBr)cm$^{-1}$: 3250, 1700, 1435, 1325, 1155
MS(m/z): 435 (M+)

EXAMPLE 52

4-[2-(2-naphthylsulfonylaminomethyl)indan-5-yl]butanoic acid:

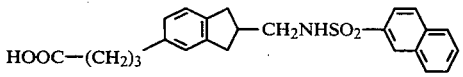

Melting point: 165°–670° C. (aqueous ethanol)
IR(KBr)cm$^{-1}$: 3255, 1695, 1155
MS(m/z): 423 (M+)

EXAMPLE 53

Formulation of Preparation Example 1:

| | |
|---|---|
| Compound of Example 1 | 20 g |
| Lactose | 315 g |
| Corn starch | 125 g |
| Crystalline cellulose | 25 g |

The ingredients indicated above were blended to form a uniform mixture, to which 200 ml of 7.5% aqueous hydroxypropylcellulose solution was added, and then the obtained mixture was granulated with an extruder equipped with a screen of 0.5 mm in diameter. Immediately thereafter, the granules were rounded with a marumerizer and dried to obtain a granule preparation.

EXAMPLE 54

Formulation of Preparation Example 2:

| | |
|---|---|
| Compound of Example 24 | 20 g |
| Lactose | 100 g |
| Corn starch | 36 g |
| Crystalline cellulose | 30 g |
| Carboxymethylcellulose calcium | 10 g |
| Magnesium stearate | 4 g |

The ingredients indicated above were blended to form a uniform mixture, and prepared into tablets each weighing 200 mg with a single-punch tableting machine equipped with a die of 7.5 mm in diameter.

EXAMPLE 55

Formulation of Preparation Example 3:

| | |
|---|---|
| Compound of Example 40 | 40 g |
| Lactose | 232 g |
| Corn starch | 108 g |
| Polyvinyl pyrrolidone | 20 g |

The ingredients indicated above were blended to form a uniform mixture, to which 180 ml of 70%(v/v) isopropyl alcohol was added, and formed into granules with an extruder equipped with a screen of 0.8 mm in diameter. Immediately thereafters, the obtained granules were rounded with a marumerizer and dried. The granules were placed in No. 2 hard gelatin capsule to prepare a capsule preparation, each content weighing 240 mg.

TEST EXAMPLES

Test 1

Inhibitory effect on U46619 induced contraction in rat aorta:

The thoracic aorta of a SD male rat (Charles River Co., Ltd.) was removed and prepared a rectangular sample which had a long side running in the parallel direction of the circular muscle. The sample was kept at 37° C., bubbled with 95% oxygen gas containing 5% $CO_2$, and suspended in a 10 ml organ bath filled with a Krebs-Henseleit solution at 2 g resting tension. $10^{-7}$ M of U46619 which is a stable active substance of $TXA_2$ was added portionwise. After the contraction responses were stabilized, the test compound was added to the organ bath, and its antagonism was evaluated. A concentration-relaxation curve was obtained, to which was applied a logit method to obtain $pIC_{50}$ values. The results are shown in Table 1.

TABLE 1

| Test Compounds | $pIC_{50}$ |
|---|---|
| Compound of Example 1 | 7.89 |
| Compound of Example 24 | 8.52 |
| Compound of Example 25 | 6.50 |
| Compound of Example 29 | 7.50 |
| Control compound* | 6.37 |

*4-(2-phenylsulfonylaminoethyl)phenoxy acetic acid

From the data in Table 1, it is understood that any of those which were added with compounds of the present invention show excellent antagonistic action.

Test 2

Human platelet aggregation inhibitory action (in vitro):

Blood samples were collected from healthy humans. 9 parts by volume of the collected blood was mixed with 1 part by volume of an aqueous 3.8%(W/v) trisodium citrate, and the mixture was subjected to centrifugal separation for collecting the supernatant-to prepare a platelet rich plasma (PRP). A further centrifugation was-performed to separate a platelet poor plasma (PPP). PRP was diluted with PPP to adjust the number of platelets to approximately $4 \times 10^5$ cells/ml. Subsequently, 200 micro liters of PRP were added with the blood sample and 25 micro liters of an equimolar aqueous sodium hydrogencarbonate solution, and stirred for 2 minutes at 37° C. Thereafter, U46619 was added thereto for inducing platelet aggregation. The platelet aggregation was measured in accordance with a Born's method ("Nature", vol 194, page 927 (1962)), and inhibition against the platelet aggregation was examined. The platelet aggregation inhibitory action of the test compounds was expressed as the $IC_{50}$ value (concentration required for inhibiting the platelet aggregation induced by 1 μM of U46619 by 50%). The data are shown in Table 2.

TABLE 2

| Test compounds | $IC_{50}$ (μM) |
|---|---|
| Compound of Example 1 | 0.72 |
| Compound of Example 24 | 0.77 |
| Compound of Example 25 | 2.45 |
| Compound of Example 30 | 0.31 |
| Compound of Example 33 | 0.85 |
| Compound of Example 34 | 0.60 |
| Compound of Example 40 | 1.12 |
| Control compound* | 2.53 |

*4-(2-phenylsulfonylaminoethyl)phenoxy acetic acid

From the data in Table 2, it is understood that the compounds according to the present invention show excellent platelet aggregation inhibitory action.

Test 3

Toxicity Test: Groups of 4–5 week old ICR mice (Charles River Co., Ltd.), each group consisting of 10 mice, were provided for the test. The compounds obtained in aforementioned Examples were respectively suspended in 10% gum arabic and each was orally administered to the rats in a dosage of 300 mg/kg. The rats were observed for 7 days. No death was found under the above conditions.

INDUSTRIAL APPLICABILITY

Since the present compounds have excellent $TXA_2$ antagonism and are very safe, they have a wide utility in the medical field such as in the treatment and prevention of various diseases caused by $TXA_2$, such as embolism and thrombosis, including cerebral thrombosis, coronary thrombosis, pulmonary embolism, chronic arterial obstruction, thromboangiitis, and also in the treatment, alleviation and prevention of myocardial ischemia, angina pectoris, coronary contraction, cerebrovascular contraction after subarachnoidal hemorrhage, cerebral hemorrhage, asthma, and the like.

We claim:

1. An indan derivative represented by the formula (1) or a pharmaceutically acceptable salt thereof:

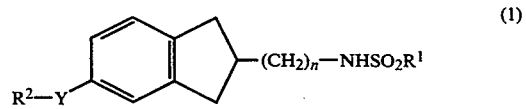

(1)

wherein $R^1$ represents an alkyl having 1–12 carbon atoms, benzyl, styryl, naphthyl, optionally substituted phenyl or optionally substituted thienyl; $R^2$ represents carboxyl, or alkoxycarbonyl, wherein the alkoxy moiety has 1–4 carbon atoms;

Y represents —(CH$_2$)$_p$— (wherein p represents an integer of 0 to 5), —CO—(CH$_2$)$_q$~, —CH(OH)—(CH$_2$)$_q$~, (wherein q represents an integer of 1 to 4, and the symbol ~ represents a linkage to R$^2$), oxymethylene or ethylene; and n represents an integer of 1 to 4.

2. A thromboxane antagonist composition containing, as its active ingredient, an indan derivative represented by the formula (1) or a pharmaceutically acceptable salt thereof:

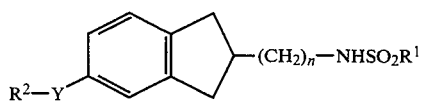

wherein R$^1$ represents an alkyl having 1–12 carbon atom, benzyl, styryl, naphthyl, optionally substituted phenyl or optionally substituted thienyl; R$^2$ represents carboxyl, or alkoxycarbonyl, wherein the alkoxy moiety has 1–4 carbon atoms;

Y represents —(CH$_2$)$_p$— (wherein p represents an integer of 0 to 5), —CO—(CH$_2$)$_q$~, —CH(OH)—(CH$_2$)$_q$~, (wherein q represents an integer of 1 to 4, and the symbol ~ represents a linkage to R$_2$), oxymethylene or ethylene; and n represents an integer of 1 to 4.

3. 2-[(4-Chlorophenyl)sulfonyl-aminomethyl)indan-5-yl]acetic acid.

4. A thromboxane antagonist composition containing, as its active ingredient, the compound of claim 3.

5. A method for the treatment of thrombosis, cerebral thrombosis, coronary thrombosis, pulmonary embolism, chronic arterial obstruction, thromboangitis, myocardial ischemia, angina pectoris, coronary contraction, cerebrovascular contraction after subarachnoidal hemorrhage, cerebral hemorrhage and asthma, comprising administering to an animal or human subject the thromboxane antagonist composition of claim 2.

6. A method for the treatment of thrombosis, cerebral thrombosis, coronary thrombosis, pulmonary embolism, chronic arterial obstruction, thromboangitis, myocardial ischemia, angina pectoris, coronary contraction, cerebrovascular contraction after subarachnoidal hemorrhage, cerebral hemorrhage and asthma, comprising administering to an animal or human subject the thromboxane antagonist composition of claim 4.

* * * * *